United States Patent [19]
Fiscella et al.

[11] 3,933,825
[45] Jan. 20, 1976

[54] AMINE SALTS OF ACYL LACTYLIC ACIDS

[75] Inventors: Anthony J. Fiscella, Holmdel, N.J.; Leonard Mackles, New York, N.Y.

[73] Assignee: Bristol-Myers Company, New York, N.Y.

[22] Filed: May 14, 1973

[21] Appl. No.: 360,238

[52] U.S. Cl.. 260/268 R; 260/247.2 B; 260/293.88; 260/326.2; 260/326.46; 260/398; 260/404; 260/405.5; 260/404.8; 260/484 A
[51] Int. Cl.$^2$...................................... C07D 211/12
[58] Field of Search................... 260/268 R, 293.88

[56] References Cited
UNITED STATES PATENTS 3,728,447    4/1973    Osipow ............................... 424/70

*Primary Examiner*—Anton H. Sutto
*Assistant Examiner*—P. J. Killos
*Attorney, Agent, or Firm*—Irving Holtzman; George A. Mentis; David J. Mugford

[57] ABSTRACT

Organic amine salt of acyl lactylic acids.

4 Claims, No Drawings

AMINE SALTS OF ACYL LACTYLIC ACIDS

This invention relates to organic amine salts of acyl lactylic acids. More particularly, it concerns amine salts of acyl lactylic acids which may be defined by the formula

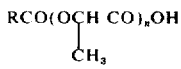

$$RCO(OCH\ CO)_nOH$$
$$|$$
$$CH_3$$

in which RCO is the acyl radical of a saturated or unsaturated fatty acid having eight to 24 carbon atoms and $n$ is a number from 1 to 10.

Acyl lactylic acids and certain inorganic salts thereof have long been known in the prior art. In this connection, by way of example of some of the prior art reference is made to U.S. Pat. Nos. 2,744,825 and 2,789,992. In addition, mention may be made of a three part article entitled "Fatty Acid Lactylates" by L. I. Osipow et al. appearing in Drug and Cosmetic Industry, March, April and May 1969.

It has now been found, however, that the organic amine salts of said acyl lactylic acids have exceptional properties which enables them to be used in a variety of applications in consumer products. For example, it has been found that amine salts function as anionic surfactants that have exceptional foaming properties. Furthermore, these materials are, in general, soluble in both water and organic solvents, e.g., mineral oil and propellants. The latter property makes it possible to incorporate these amine salts directly into the propellant systems of aerosol products and to provide non-aqueous foaming systems.

The organic amine salts of the present invention have a large number and variety of uses. Thus, they may be employed as a surfactant and/or foaming agent in aerosol foam shampoos, in medicated acne foam cleaners, in aerosol toothpaste compositions, in non-aqueous self-foaming shampoo gel compositions, etc. These uses form the subject matter of some copending patent applications. (See, for example, application Ser. No. 334,556 filed Feb. 22, 1973 now abandoned).

The amine salts of the present invention may be prepared by first forming a solution of the appropriate acyl lactylic acid in a solvent, e.g., ethanol and then adding the amine to this solution. After completion of the addition of the amine, the solution is stirred for an additional period of time until the reaction is completed. The solvent is then removed in vacuo and at temperatures which are slightly above room temperature.

The lactylic acid compositions employed in accordance with the invention in the preparation of the fatty acid esters used herein are easily obtained from the lactic acid of commerce which is usually in the form of an 85% aqueous solution. The free water is readily removed and the condensation initiated by heating such solutions at 100°–110°C for several hours with or without the aid of vacuum. Lactic acid upon heating at 180°–220°C with or without catalysts polymerizes readily and progressively to form polylactylic acids. The progress of the polymerization can readily be followed by titration of samples withdrawn from the reaction vessel to determine the free acidity and average equivalent or molecular weight. Therefore, by terminating heating at the appropriate time it is possible to obtain anhydrous products containing any desired average number of lactyl groups, from one upward.

The esters used in this invention in preparing the amine salts can be prepared by conventional esterification methods, but it has been found advantageous to prepare them by heating the halide of the long chained fatty acid with lactylic acid composition of the desired degree of polymerization under substantially anhydrous conditions. The polymeric latylic acid compositions employed normally contain lactic acid of varying degrees of polymerization and consequently the degree of polymerization of any particular polymeric composition employed is an average degree of polymerization. Such average degree is easily determined by ascertaining the free acidity of the product and the average equivalent or molecular weight. It has been found that during esterification reaction with the fatty acid halides, the degree of polymerization of the lactylic acid composition may alter to a slight degree in view of a further polymerization or depolymerization during such reaction.

The fatty acid halides that may be used to prepare the esters employed in synthesizing the present amine salts are quite varied. These are ordinarily selected with the view of producing esters whose amine salts are soluble both in water and in organic solvent (e.g., normally gaseous hydrocarbon or halogenated hydrocarbon which may serve as propellants in aerosol systems). These will be of the formula RCOCl in which RCO— is the acyl radical of saturated or unsaturated fatty acid having from eight to 24 carbon atoms and preferably from 16 to 22 carbon atoms. Typical among these acyl radicals that may be mentioned are capryl, lauroyl, stearoyl, oleoyl, palmityl, myristyl, behenyl, arachidyl, linoleyl.

The organic amines that can be used in preparing the present amine salts are quite varied and quite numerous. However, they will usually be selected with the end view in mind of producing a compound which is both water soluble and organic solvent soluble. Any amine which will produce an amine salt with the acyl lactylic acid that has these solubility characteristics are especially suitable for use in the present invention.

The amines that are particularly useful for forming amine salts in accordance with this invention are secondary and tertiary amines. These may take the form of aliphatic, cycloaliphatic or aromatic amines, or may be amines of the type in which the secondary amine nitrogen forms part of the ring of a five or six member saturated nitrogen heterocyclic radical, e.g., piperidine, piperazine, morpholine, pyrolidine. In the case in which the amines are aliphatic amines, they are preferably secondary or tertiary lower alkyl amines having one to five carbons in each alkyl chain or lower alkanol amines containing one to five carbon atoms and one to three hydroxy groups. By way of illustrating these amines, mention may be made of dimethylamine, trimethylamine, diethylamine, triethylamine, di-n-propylamine, tri-n-propylamine, diethanolamine, triethanolamine, diisopropanolamine, triisopropanolamine.

The following examples are given to further illustrate the present invention. It is to be understood, however, that the invention is not limited thereto.

EXAMPLE 1

Triethanolammonium lauroyl (1.2) Polylactylate

A reaction flask containing a mixture of 50.4 grams (0.40 moles) of a lactylic acid preparation, prepared as previously described, with an average equivalent weight of 126 (1.5 lactyl groups per mole) and 87.4 grams (0.40 moles) of lauroyl chloride was heated over a mineral oil bath to 50°C while stirring to initiate the reaction. After the reaction had subsided, as evidenced by a reduction in the original copious evolution of HCl, the temperature of the reaction mixture was raised to and maintained at 70°C for about 4 hours when the evolution of HCl ceased. Thereafter the temperature was raised to 130°C to insure complete reaction.

The product was a thick amber oil having an average equivalent weight of 286.4 (1.2 lactyl groups per mole).

A solution containing 71.6 grams (0.4 moles) of this acid in 200 ml of absolute ethanol was prepared and a solution of 59.7 g (0.4 moles) of triethanolamine in 150 ml of absolute ethanol was added to it in a slow stream with stirring. After addition was complete, the solution was stirred for 20 minutes and the alcohol was removed below 40°C in vacuo leaving triethanolammonium lauroyl lactylate as an amber paste.

The following examples are given in tabular form. The procedure employed is the same as that given for Example 1; however, there is a variation from example to example with respect to the acyl halide employed in acylating the lactylic acid or the amine utilized in preparing the amine salt.

TABLE I

| Ex. No. | Acyl Chloride | Amine | Value of "n" in lactylic acid formula $H(O\ CH\ CO)_nOH$ employed $CH_3$ |
|---|---|---|---|
| 2 | stearoyl chloride | triethanol-amine | n = 1.2 Av. |
| 3 | myristoyl chloride | " | " |
| 4 | oleoyl chloride | " | " |
| 5 | lauroyl chloride | diethanol-amine | " |
| 6 | " | triethylamine | " |
| 7 | " | triisopropyl-amine | " |
| 8 | " | triisopropanol-amine | " |
| 9 | " | piperidine | " |
| 10 | " | piperazine | " |
| 11 | " | morpholine | " |
| 12 | " | pyrollidine | " |

EXAMPLE 13

Preparation of stearyl (8.5) polylactylic acid ester TEA salt

A mixture of 127.0 grams of a polylactylic acid composition having an average equivalent weight of 803.86 (10.9 lactyl groups per mole) and 48.01 grams of stearyl chloride was gradually heated while stirring over an oil bath over a period of several hours to a temperature of 180°C at which time the evolution of HCl ceased. The product was brownish in color and semi-crystalline but of distinctly lipoidal character.

This product was purified by dissolving it in two volumes of warm chloroform and adding 5 grams of active charcoal and a few drops of concentrated $H_2SO_4$ to the solution. After standing over night the insolubles were removed by filtration and the chloroform solution was washed several times in a separatory funnel with water to remove the water solubles. The solution was then filtered and the chloroform removed by distillation under vacuum.

The product was a light honey colored solid with an average equivalent weight of 897 (8.5 lactyl groups per mole) and a melting point of about 58°–63°C.

A solution containing 71.6 grams (0.4 moles) of this acid in 200 ml of absolute ethanol was prepared and a solution of 59.7 grams (0.4 moles) of triethanolamine in 150 ml of absolute ethanol was added to it in a slow stream with stirring. After addition was complete the solution was stirred for 20 minutes and the alcohol was removed below 40°C in vacuo leaving triethanlammonium stearyl (8.5) polylactylate.

The following examples are also given in tabular form. The procedure employed is the same as that given in Example 13; however, there is a variation from Example to Example with respect to the acyl halide employed in acylating the lactylic acid employed or the amine utilized in preparing the amine salt.

TABLE II

| Ex. No. | Acyl Chloride | Amine | Value of "n" in lactylic acid formula $H(O\ CH\ CO)_nOH$ employed $CH_3$ |
|---|---|---|---|
| 14 | lauroyl chloride | triethanol-amine | n = 8.5 Av. |
| 15 | myristoyl chloride | " | " |
| 16 | oleoyl chloride | " | " |
| 17 | lauroyl chloride | diethanolamine | " |
| 18 | " | triethylamine | " |
| 19 | " | triisopropyl- | " |

TABLE II-continued

| Ex. No. | Acyl Chloride | Amine | Value of "n" in lactylic acid formula H(O CH CO)$_n$OH employed CH$_3$ |
|---|---|---|---|
| 20 | " | triisopropanol- amine | " |
| 21 | " | piperidine | " |
| 22 | " | piperazine | " |
| 23 | " | morpholine | " |
| 24 | " | pyrollidine | " |

Although the invention has been described with reference to specific forms thereof, it will be understood that many changes and modifications may be made without departing from the spirit of this invention.

What is claimed is:

1. Water soluble, organic solvent soluble piperidine or pyrralidine salts of acyl lactylic acids of formula

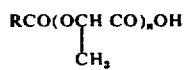

wherein RCO is the acyl radical of a saturated or unsaturated fatty acid having eight to 24 carbon atoms, and $n$ is a number from 1 to 10.

2. The salts according to claim 1 wherein RCO— is an acyl radical having 16 to 22 carbon atoms and $n$ is a number from about 1 to 8.5.

3. Water soluble, organic solvent soluble piperazine salts of acyl lactylic acids of formula

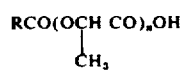

wherein RCO is the acyl radical of a saturated or unsaturated fatty acid having eight to 24 carbon atoms, and $n$ is a number from 1 to 10.

4. The salts according to claim 3 wherein RCO— is an acyl radical having 16 to 22 carbon atoms and $n$ is a number from about 1 to 8.5.

* * * * *